(12) United States Patent
Wang

(10) Patent No.: US 11,444,253 B2
(45) Date of Patent: Sep. 13, 2022

(54) THERMALLY ACTIVATED DELAYED FLUORESCENT MATERIAL AND PREPARATION METHOD THEREOF

(71) Applicant: Wuhan China Star Optoelectronics Semiconductor Display Technology Co., Ltd., Wuhan (CN)

(72) Inventor: Bo Wang, Wuhan (CN)

(73) Assignee: Wuhan China Star Optoelectronics Semiconductor Display Technology Co., Ltd., Wuhan (CN)

( * ) Notice: Subject to any disclaimer, the term of this patent is extended or adjusted under 35 U.S.C. 154(b) by 281 days.

(21) Appl. No.: 16/639,593

(22) PCT Filed: Jan. 3, 2020

(86) PCT No.: PCT/CN2020/070311
§ 371 (c)(1),
(2) Date: Feb. 17, 2020

(87) PCT Pub. No.: WO2021/088243
PCT Pub. Date: May 14, 2021

(65) Prior Publication Data
US 2021/0384447 A1 Dec. 9, 2021

(30) Foreign Application Priority Data
Nov. 6, 2019 (CN) .......................... 201911075240.7

(51) Int. Cl.
| | |
|---|---|
| *C07D 413/14* | (2006.01) |
| *C07K 11/02* | (2006.01) |
| *H01L 51/00* | (2006.01) |
| *C09K 11/02* | (2006.01) |
| *C09K 11/06* | (2006.01) |
| *H01L 51/50* | (2006.01) |

(52) U.S. Cl.
CPC ........ *H01L 51/0074* (2013.01); *C07D 413/14* (2013.01); *C09K 11/02* (2013.01); *C09K 11/06* (2013.01); *H01L 51/0067* (2013.01); *H01L 51/0071* (2013.01); *H01L 51/0072* (2013.01); *C09K 2211/1018* (2013.01); *H01L 51/5012* (2013.01)

(58) Field of Classification Search
CPC .............................. C07D 413/14; C09K 11/02
See application file for complete search history.

(56) References Cited

U.S. PATENT DOCUMENTS

| | | | |
|---|---|---|---|
| 2017/0271601 | A1 | 9/2017 | Aspuru-Guzik et al. |
| 2018/0269408 | A1 | 9/2018 | Yang et al. |
| 2019/0036035 | A1 | 1/2019 | Yang et al. |
| 2021/0280797 | A1 | 9/2021 | Luo et al. |

FOREIGN PATENT DOCUMENTS

| | | |
|---|---|---|
| CN | 105585577 | 5/2016 |
| CN | 106661001 | 5/2017 |
| CN | 107759774 | 3/2018 |
| CN | 108358905 | 8/2018 |
| CN | 110105330 | 8/2019 |
| CN | 110128443 | 8/2019 |

OTHER PUBLICATIONS

Wang et al. "Studies on the Palladium-Catalyzed Coupling of Acid Chlorides and Aromatic Halides With Tributylheterocyclictin Reagents", Acta Chimica Sinica, 51: 393-398, Jan. 1993. & English Abstract.

*Primary Examiner* — Yong S. Chong

(57) ABSTRACT

A thermally activated delayed fluorescent material includes a compound having structural formula (I) as follows:

A-D          (I).

A is an electron acceptor and D is an electron donor. In addition, a method of preparing a thermally activated delayed fluorescent material and an organic light emitting diode display device using the thermally activated delayed fluorescent material as luminescent host material are provided. The organic light emitting diode display device includes an anode, a cathode, and an organic functional layer disposed between the anode and the cathode. The organic functional layer includes the thermally activated delayed fluorescent material having a structural formula (I).

2 Claims, 2 Drawing Sheets

THERMALLY ACTIVATED DELAYED FLUORESCENT MATERIAL AND PREPARATION METHOD THEREOF

RELATED APPLICATIONS

This application is a National Phase of PCT Patent Application No. PCT/CN2020/070311 having International filing date of Jan. 3, 2020, which claims the benefit of priority of Chinese Patent Application No. 201911075240.7 filed on Nov. 6, 2019. The contents of the above applications are all incorporated by reference as if fully set forth herein in their entirety.

FIELD AND BACKGROUND OF THE INVENTION

The present invention relates to the field of organic electroluminescent materials, and more particularly, to a thermally activated delayed fluorescent material and a preparation method thereof.

Dominant guest luminescent materials are critical in determining luminous efficiency of organic light emitting diode (OLED) display devices. The luminescent guest materials used in OLED display devices are fluorescent materials. Generally, a ratio of singlet excitons to triplet excitons in the OLED display devices is 1:3, so an internal quantum efficiency (IQE) of the OLED display devices is merely 25%. Therefore, application of fluorescent electroluminescent devices is greatly limited. Phosphorescent heavy-metal complexes can achieve 100% IQE by using singlet and triplet excitons simultaneously due to spin-orbit coupling of heavy atoms. However, the commonly used heavy-metals are precious metals, such as iridium (Ir), platinum (Pt), or osmium (Os), which have high toxicity and high cost. In addition, pure organic thermally activated delayed fluorescent materials have a lowest single-triplet level difference ($\Delta EST$) which is relatively lower than ever before, so that triplet excitons can be transformed to a singlet state by reverse intersystem crossing (RISC), and are then illuminated when jumping to a ground state transition by radiation. Therefore, single and triplet excitons can be simultaneously used and can achieve 100% IQE.

As for the thermally activated delayed fluorescent materials, a high reaction rate constant of reverse intersystem enthalpy constant ($k_{RISC}$) and a high photoluminescence quantum yield (PLQY) are necessary for fabricating OLED display devices having high luminous efficiency. Currently, the thermally activated delayed fluorescent materials with the above features are still relatively lacking as compared with heavy metal complexes.

SUMMARY OF THE INVENTION

A thermally activated delayed fluorescent material comprises a compound having structural formula (I) as follows:

A-D (I), and A is an electron acceptor, D is an electron donor, and the electron acceptor comprises any one of following chemical structural formulas:

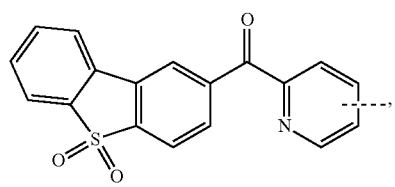

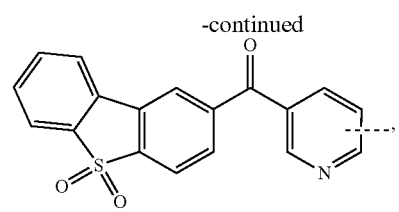

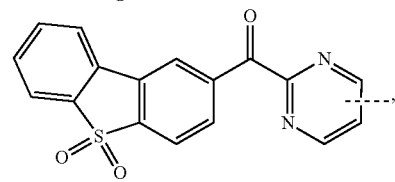

and

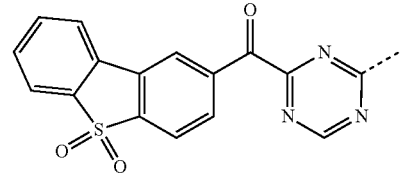

and the electron donor comprises any one of following chemical structural formulas:

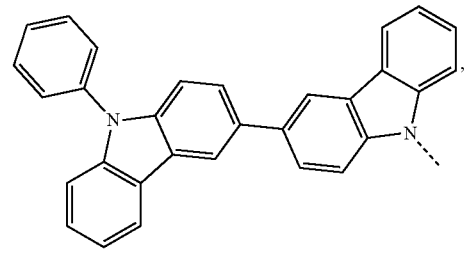

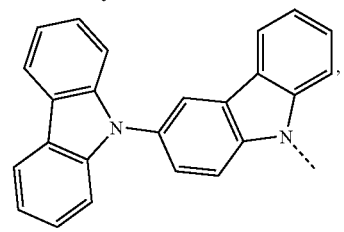

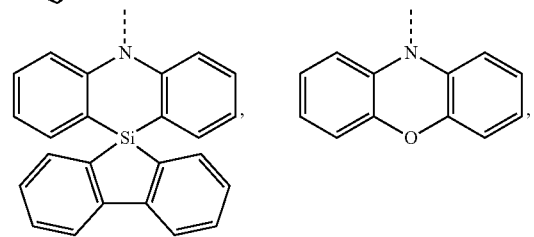

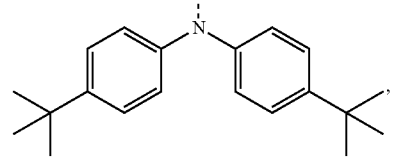

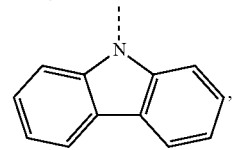

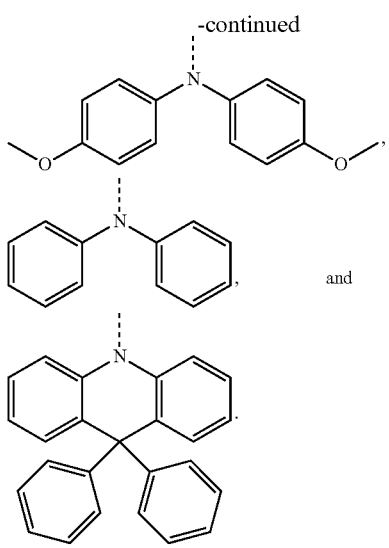

In one embodiment, the compound comprises one of following chemical structural formulas:

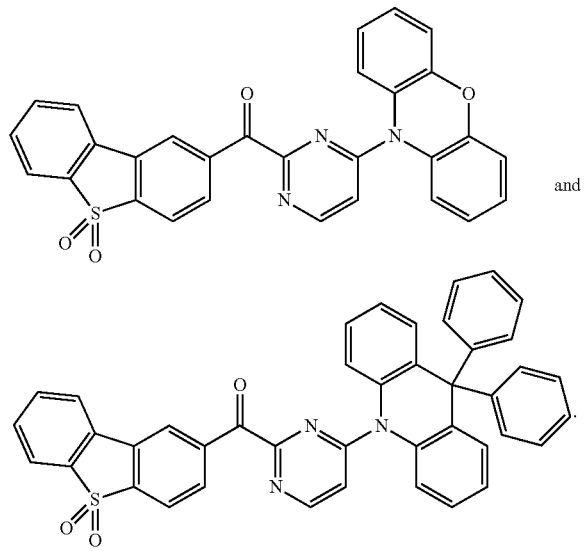

A method of preparing a thermally activated delayed fluorescent material, comprises following steps:

S1, mixing fluorobenzoyl chloride with a nitrogen-containing heterocyclic compound having a halogen substituent to obtain a mixture;

S2, adding a first compound to the mixture, and the mixture and the first compound are reacted to obtain a compound A-X, and the first compound comprises following chemical structural formulas:

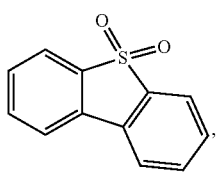 [SMILES: O=S1(=O)c2ccccc2-c2ccccc21]

and X is halogen, and A comprises any one of the following chemical structural formulas:

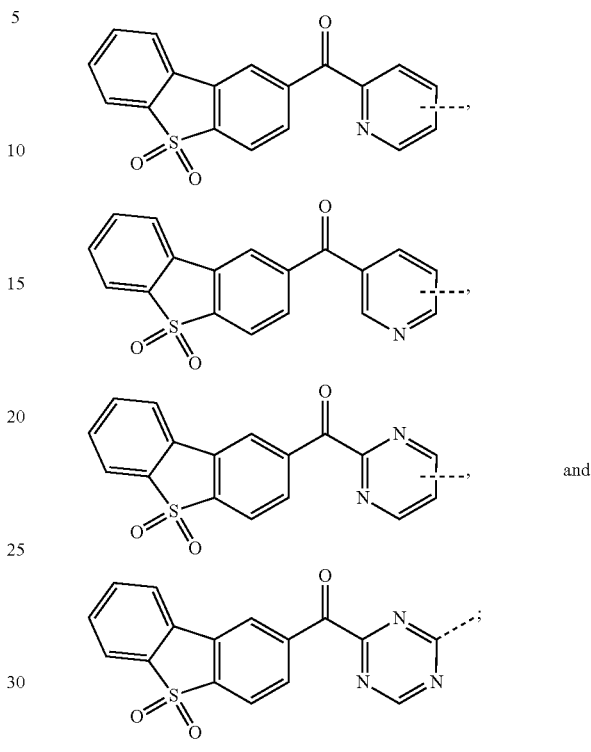

adding a compound D-H into the compound A-X followed by performing a reaction to obtain an initial product, and D comprises any one of the following chemical structural formulas:

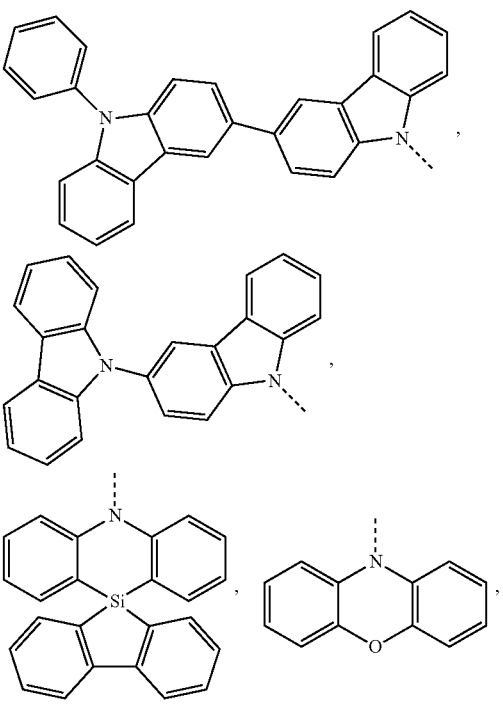

-continued

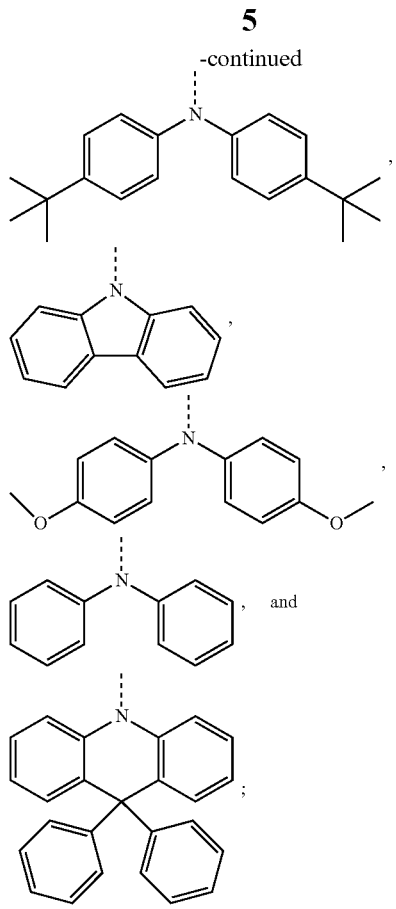

and

S3, extracting and drying the initial product to obtain the thermally activated delayed fluorescent material, and the thermally activated delayed fluorescent material comprises a compound having structural formula (I) as follows:

A-D (I).

In one embodiment, the fluorobenzoyl chloride is 4-fluorobenzoyl chloride.

In one embodiment, the nitrogen-containing heterocyclic compound having a halogen substituent is 4-fluoro-2-iodopyrimidine.

In one embodiment, the step S2 of adding the first compound to the mixture further comprises adding aluminum trichloride.

In one embodiment, the thermally activated delayed fluorescent material comprises

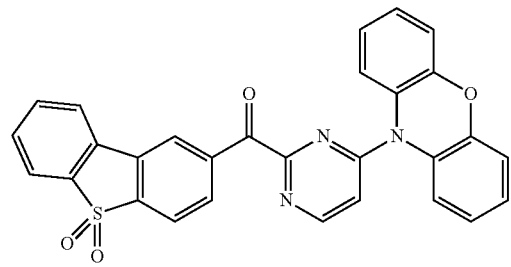

and

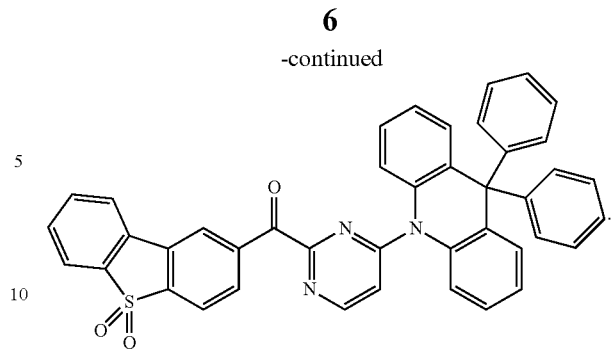

In one embodiment, the step S3 of the extracting is performed by using dichloromethane.

In one embodiment, the step S3 of the drying is performed by a drying agent, and the drying agent comprises anhydrous magnesium sulfate and anhydrous sodium sulfate.

In one embodiment, the thermally activated delayed fluorescent material is a fluorescent host material used in an organic light emitting diode display device.

A method of preparing a thermally activated delayed fluorescent material comprises following steps:

S1, mixing fluorobenzoyl chloride with a nitrogen-containing heterocyclic compound having a halogen substituent to obtain a mixture, wherein the fluorobenzoyl chloride is 4-fluorobenzoyl chloride, and the nitrogen-containing heterocyclic compound having a halogen substituent is 4-fluoro-2-iodopyrimidine;

S2, adding a first compound to the mixture, and the mixture and the first compound are reacted to obtain a compound A-X, and the first compound comprises following chemical structural formulas:

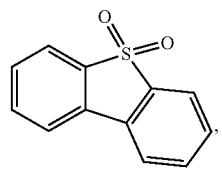 [SMILES: O=S1(=O)c2ccccc2-c2ccccc21]

and X is halogen, and A comprises any one of the following chemical structural formulas:

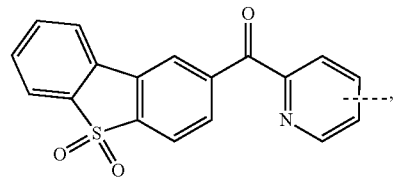

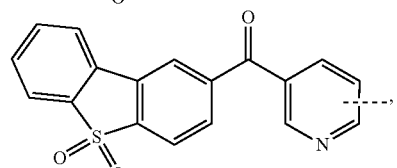

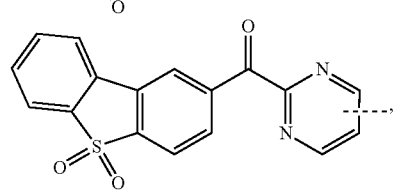

and

-continued

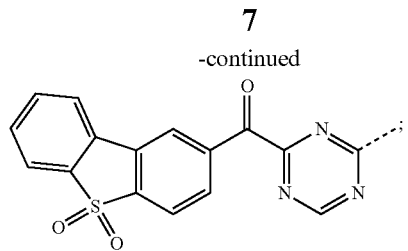

adding a compound D-H into the compound A-X followed by performing a reaction to obtain an initial product, and D comprises any one of the following chemical structural formulas:

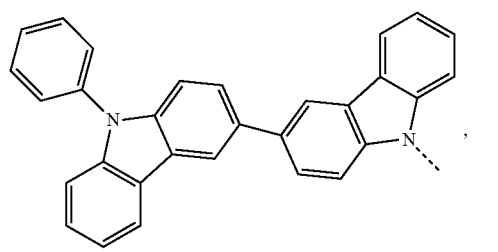

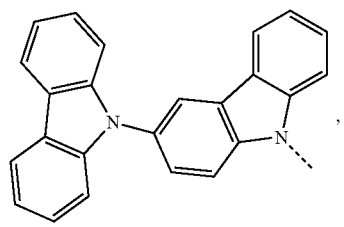

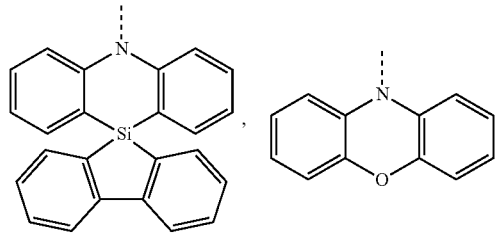

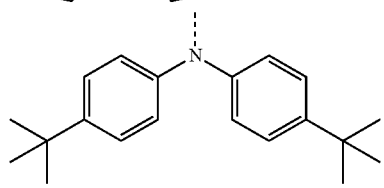

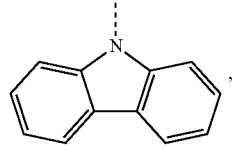

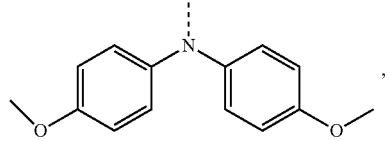

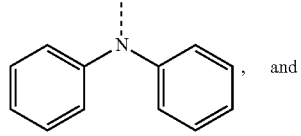, and

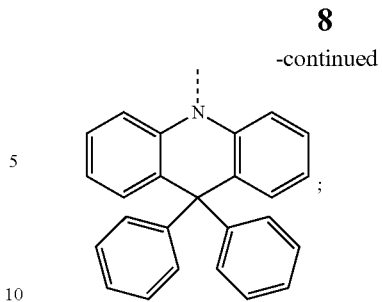

and

S3, extracting and drying the initial product to obtain the thermally activated delayed fluorescent material, and the thermally activated delayed fluorescent material comprises a compound having structural formula (I) as follows:

A-D         (I).

In one embodiment, the step S2 of adding the first compound to the mixture further comprises adding aluminum trichloride.

In one embodiment, the thermally activated delayed fluorescent material comprises

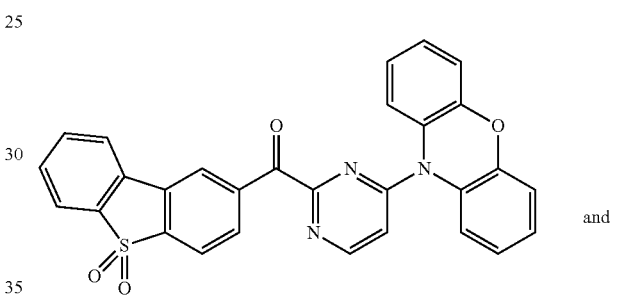 and

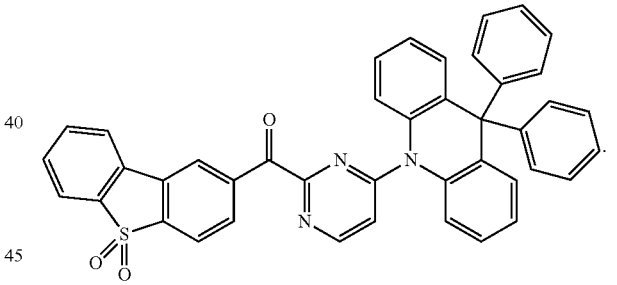.

In one embodiment, the step S3 of the extracting is performed by using dichloromethane.

In one embodiment, the step S3 of the drying is performed by a drying agent, and the drying agent comprises anhydrous magnesium sulfate and anhydrous sodium sulfate.

In one embodiment, the thermally activated delayed fluorescent material is a fluorescent host material used in an organic light emitting diode display device.

A thermally activated delayed fluorescent material is provided, and it can reduce the energy level difference of the lowest single-triplet state, and thus an organic light emitting diode display device having high luminescent efficiency is achieved.

DESCRIPTION OF SPECIFIC EMBODIMENTS OF THE INVENTION

Figure 1:
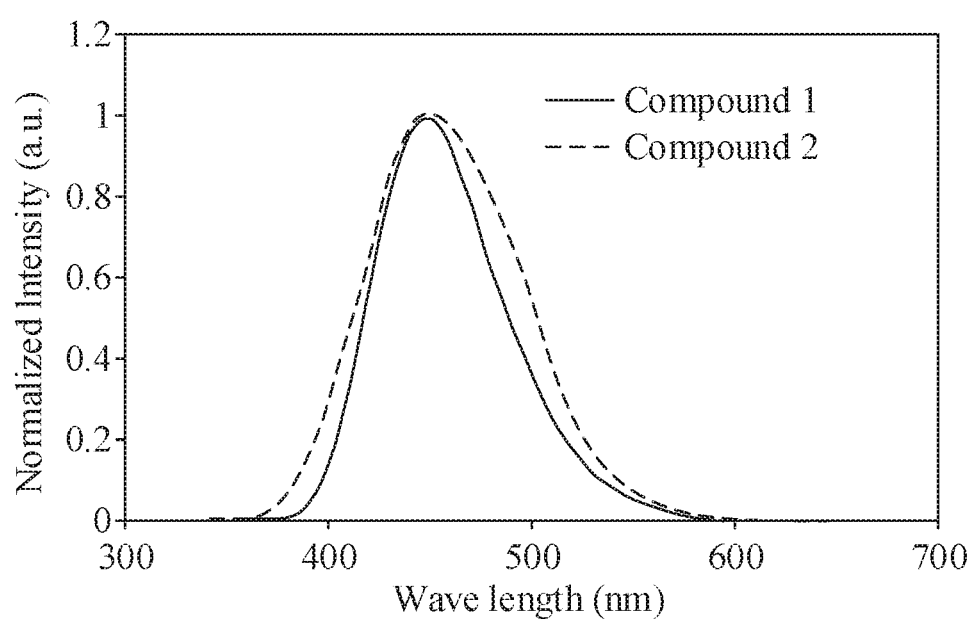
FIG. 1 is a photoluminescence spectrum of a thermally activated delayed fluorescent material according to one embodiment of the present invention.

Generally, a thermally activated delayed fluorescent material has a molecular structure in which an electron donor and an electron acceptor are combined. A thermally activated delayed fluorescent material having different electron donors and electron acceptors is used to manufacture an organic light emitting diode device with high luminous efficiency.

A thermally activated delayed fluorescent material, comprising a compound having structural formula (I) as follows:

A-D    (I).

A is an electron acceptor and D is an electron donor, and the electron acceptor comprises any one of following chemical structural formulas:

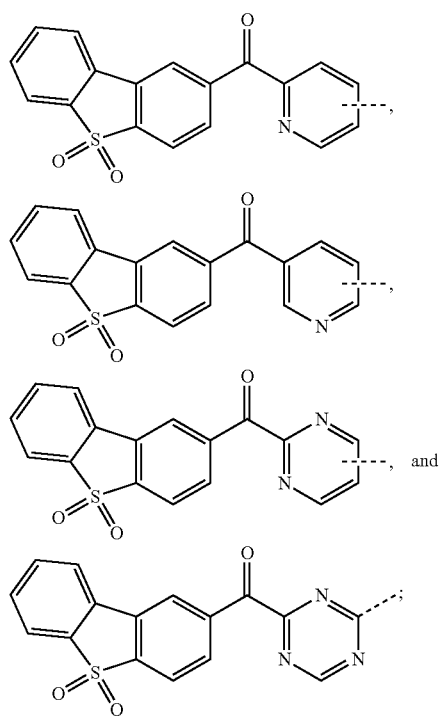

and the electron donor comprises any one of following chemical structural formulas:

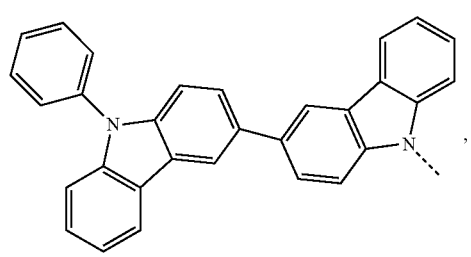

-continued

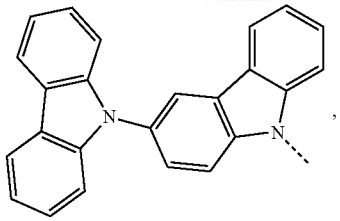

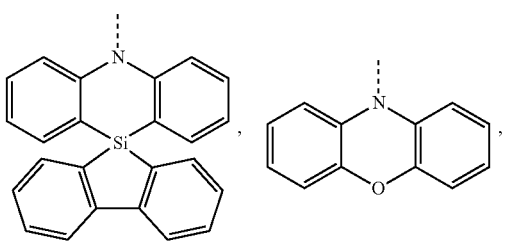

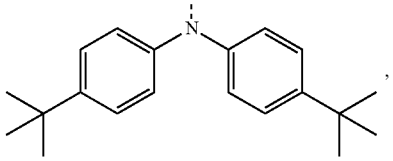

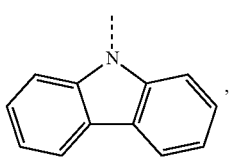

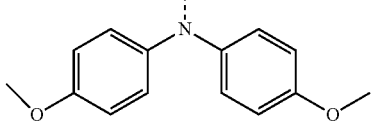

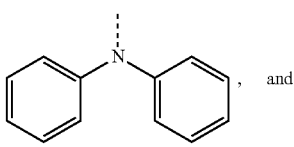

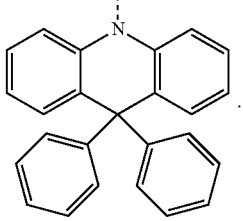

Preferably, the electron acceptor is selected from the group consisting of

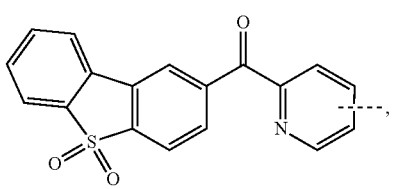

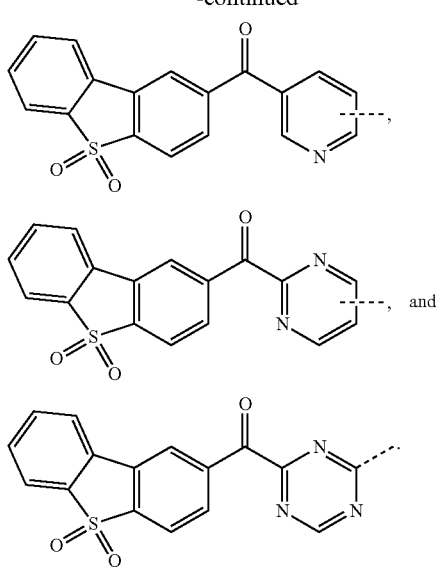

Preferably, the electron donor comprises any one of following chemical structural formulas:

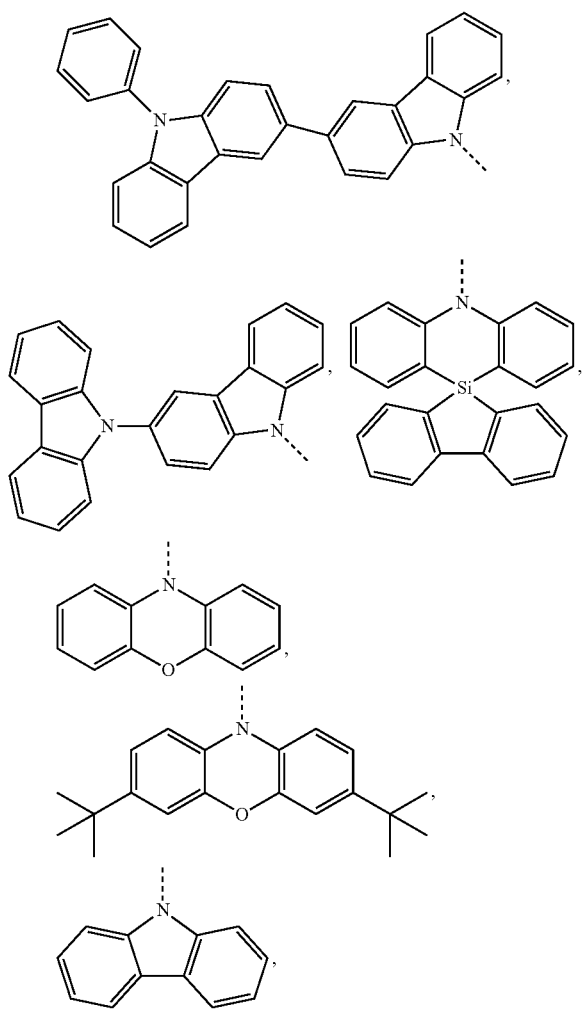

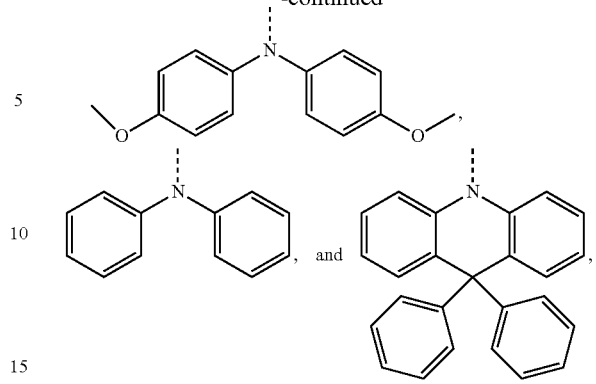

In order to allow skilled persons in the art to understand the synthesis process of the thermally activated delayed fluorescent material in the embodiments of the present invention, the synthesis steps of the thermally activated delayed fluorescent material in different embodiments of the present invention are further described below. Many alternatives, modifications, and variations are apparent to those skilled persons in the art. Therefore, not all the compounds of the examples of the present invention are described herein.

In another embodiment, a method of preparing a thermally activated delayed fluorescent material comprises following steps:

S1, mixing fluorobenzoyl chloride with a nitrogen-containing heterocyclic compound having a halogen substituent to obtain a mixture;

S2, adding a first compound to the mixture, and the mixture and the first compound are reacted to obtain a compound A-X, wherein the first compound comprises following chemical structural formulas:

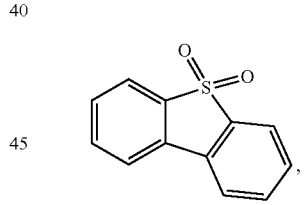

and X is halogen, and A comprises any one of the following chemical structural formulas:

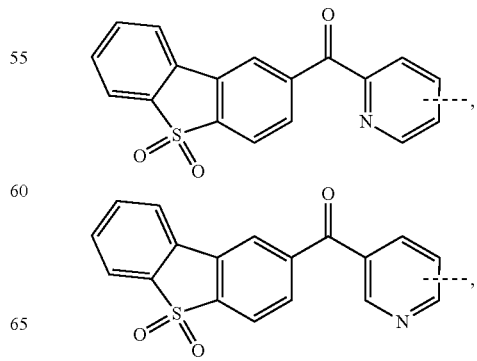

-continued

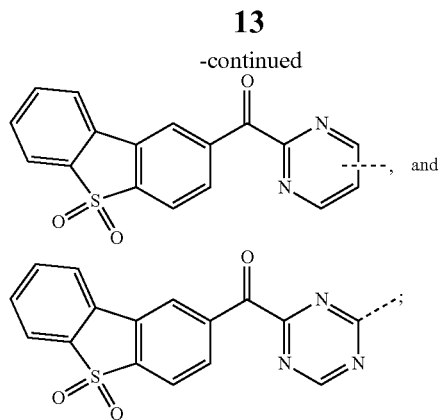
and

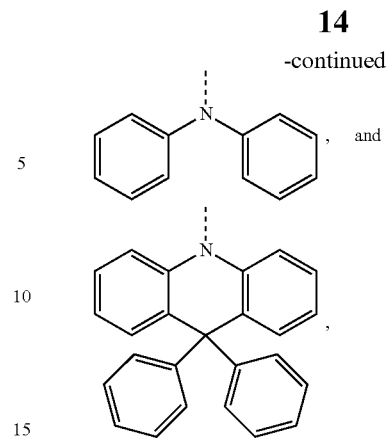
and adding a compound D-H into the compound A-X followed by performing a reaction to obtain an initial product, and D comprises any one of the following chemical structural formulas:

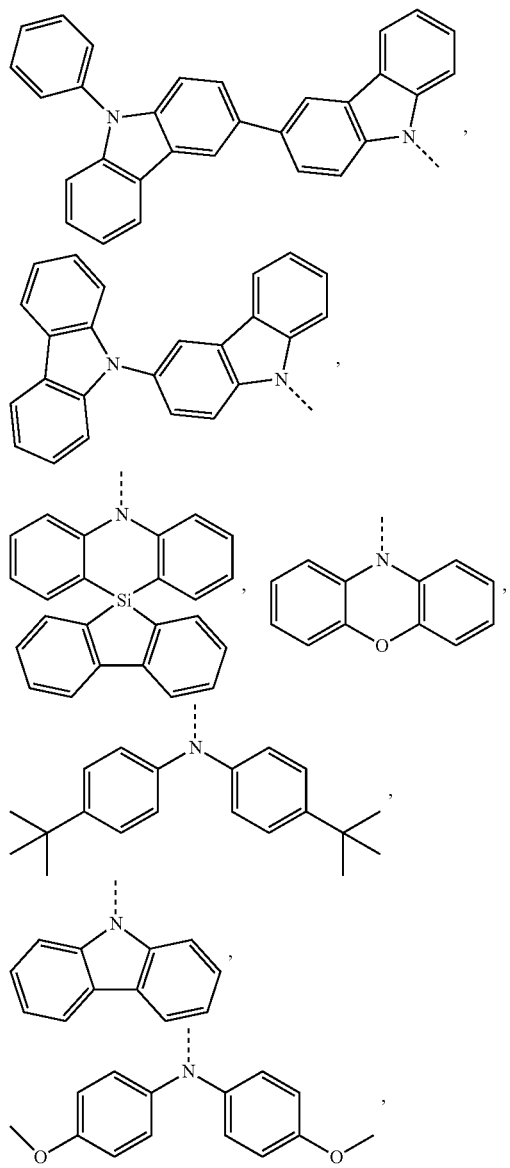

and an initial product is obtained after reaction; and S3, extracting and drying the initial product to obtain the thermally activated delayed fluorescent material, and the thermally activated delayed fluorescent material comprises a compound having structural formula (I) as follows:

A-D                         (I).

The thermally activated delayed fluorescent material comprises

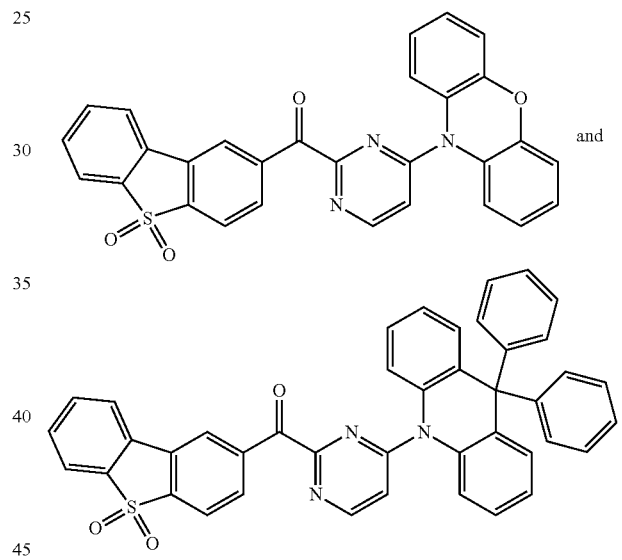

In addition, the thermally activated delayed fluorescent material is a fluorescent host material used in an organic light emitting diode display device. In detail, the step S2 of adding the first compound to the mixture further comprises adding aluminum trichloride. In the step S3 of the drying is performed by a drying agent, and the drying agent comprises anhydrous magnesium sulfate and anhydrous sodium sulfate.

In the first embodiment, the synthesis steps for compound I

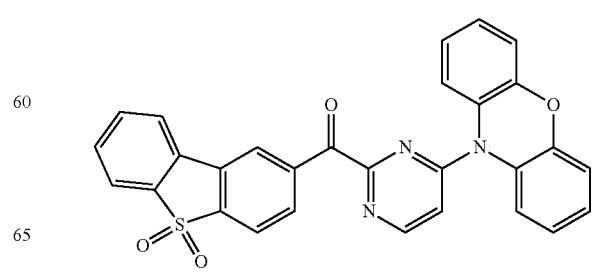

are described as follows:

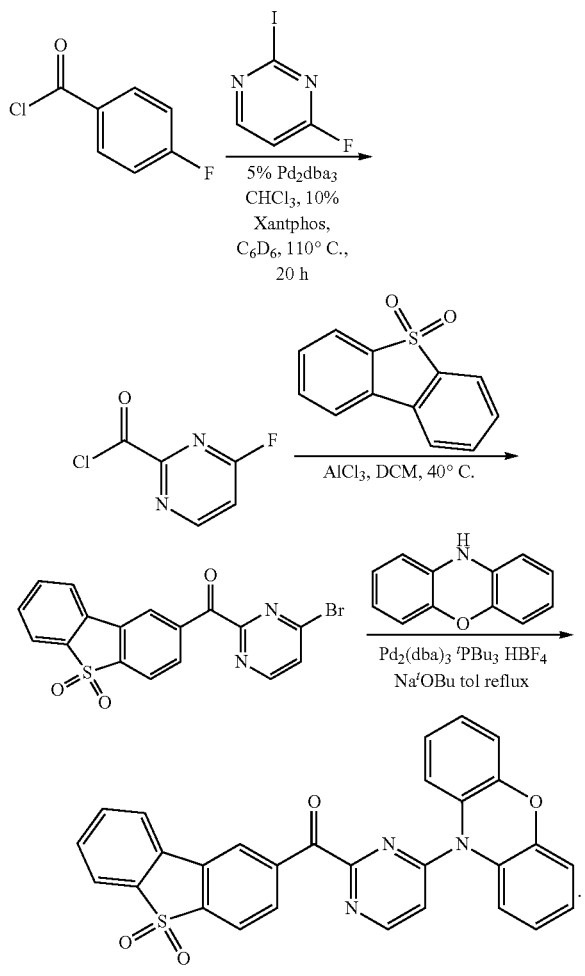

First of all, 4-fluorobenzoyl chloride (1 mole), 4-fluoro-2-iodopyrimidine (1 mole), 5% Pd₂dba₃·CHCl₃ (0.05 mole), 10% Xantphos (0.1 mole), and C₆D₆ are added into a reaction flask, and reacted at 110° C. for 20 hours to form an initial product

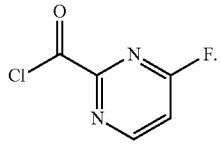

Next, aluminum trichloride (1.60, 12 mmol) and compound

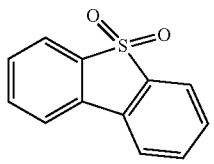 [SMILES: O=S1(=O)c2ccccc2-c2ccccc21]

are added into a continuously stirring solution of dehydrated dichloromethane (50 mL) and kept in an ice bath for 15 minutes. Then, the reaction mixture is heated to room temperature and stirred for 3 hours. At the same time, the quenching reaction is performed with ice water and hydrochloric acid (30 mL, volume ratio 2:1) and extracted several times with dichloromethane. The combined organic solution is washed with water for two times, and then it is dried by using anhydrous magnesium sulfate. After filtrating the combined organic solution and evaporating the solvent under reduced pressure, a residue is obtained. Then, it is purified by silica gel column chromatography (dichloromethane:petroleum ether, volume ratio 1:3) to obtain 3.51 g of a white solid. The white solid is (4-bromopyrimidin-2-yl)5,5-dioxodibenzo [b, d] thiophen-2-yl)methanone

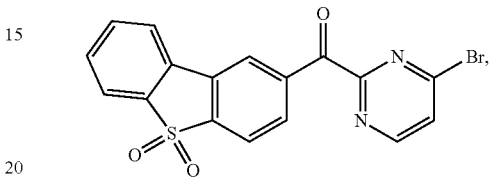

and a yield of product is 96%.

Next, (4-bromopyrimidin-2-yl) (5,5-dioxodibenzo [b, d] thiophen-2-yl) methanone (3.208 g, 8 mmol), 10H-phenoxa (1.61 g, 8.8 mmol), Pd₂(dba)₃ (0.15 g, 0.16 mmol), tPBu₃ HBF₄ (0.18 g, 0.64 mmol) and sodium tert-butoxide (1.92 g, 20 mmol) are added into a 100 mL reaction flask, and pumping with argon and adding anhydrous toluene (40 mL). Under argon atmosphere, the reaction is refluxed overnight. After cooling, it is repeatedly extracted for three times with dichloromethane (DCM) and washed with water for three times, and then dried by using anhydrous sodium sulfate. Next, it is filtrated and concentrated. Finally, it is purified by silica gel column chromatography and petroleum ether/dichloromethane (volume ratio 8:1) is used as eluent to obtain 3.42 g of white solid compound I

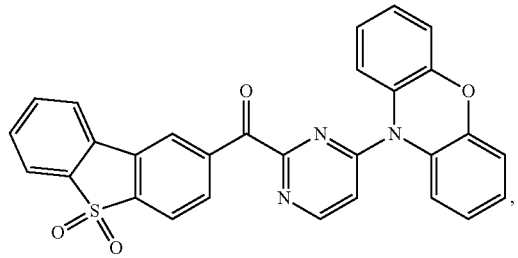 [SMILES: O=C(c1ccc2c(c1)-c1ccccc1S2(=O)=O)c1nccc(N2c3ccccc3Oc3ccccc32)n1]

and a yield of product is 85%. Product identification data: HRMS [M+H]+ calcd. for C₂₉H₁₇N₃O₄S: 503.09. found: 504.08.

In the second embodiment, the synthesis steps for compound II

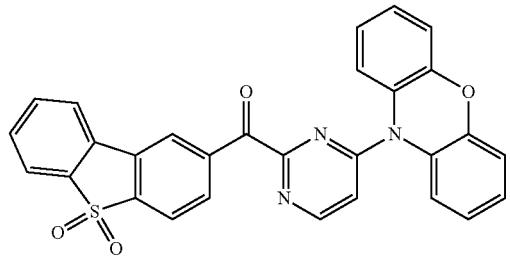 [SMILES: O=C(c1ccc2c(c1)-c1ccccc1S2(=O)=O)c1nccc(N2c3ccccc3Oc3ccccc32)n1]

are described as follows:

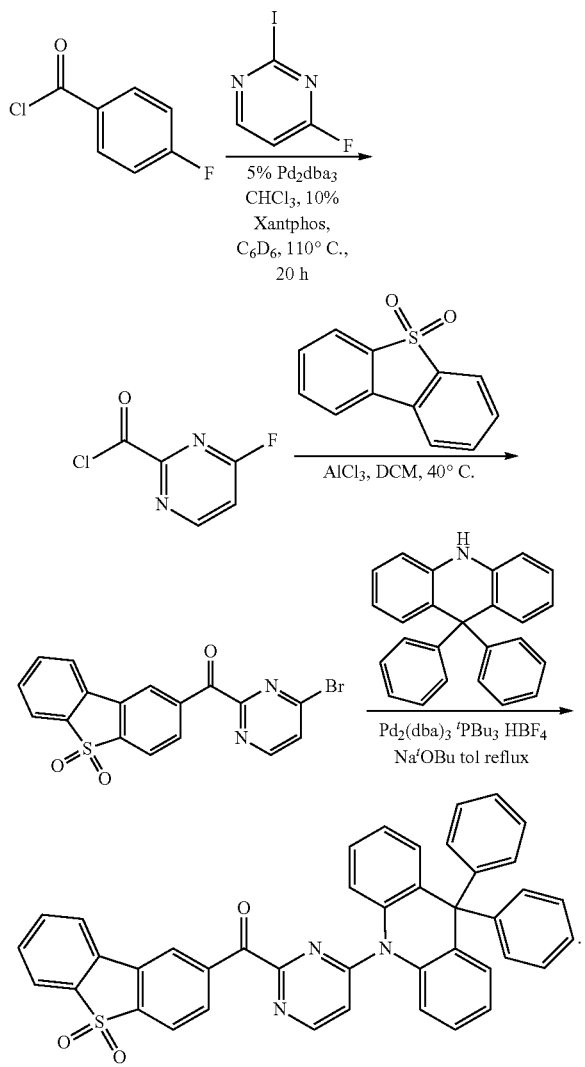

First of all, 4-fluorobenzoyl chloride (1 mole), 4-fluoro-2-iodopyrimidine (1 mole), 5% Pd$_2$dba$_3$·CHCl$_3$ (0.05 mole), 10% Xantphos (0.1 mole), and C$_6$D$_6$ are added into a reaction flask, and reacted at 110° C. for 20 hours to form an initial product

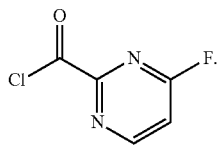

Next, aluminum trichloride (1.60, 12 mmol) and compound

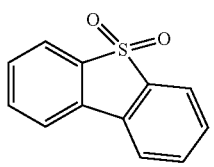 [SMILES: O=S1(=O)c2ccccc2-c2ccccc21]

are added into a continuously stirring solution of dehydrated dichloromethane (50 mL) and kept in an ice bath for 15 minutes. Then, the reaction mixture is heated to room temperature and stirred for 3 hours. At the same time, the quenching reaction is performed with ice water and hydrochloric acid (30 mL, volume ratio 2:1) and extracted several times with dichloromethane. The combined organic solution is washed with water for two times, and then it is dried by using anhydrous magnesium sulfate. After filtrating the combined organic solution and evaporating the solvent under reduced pressure, a residue is obtained. Then, it is purified by silica gel column chromatography (dichloromethane:petroleum ether, volume ratio 1:3) to obtain 3.51 g of a white solid. The white solid is (4-bromopyrimidin-2-yl)5,5-dioxodibenzo [b, d] thiophen-2-yl)methanone,

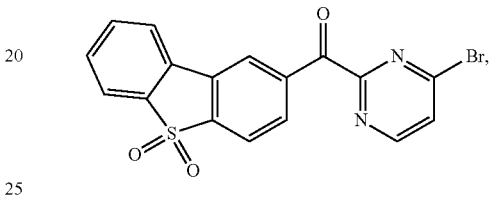

and a yield of product is 96%.

Next, (4-bromopyrimidin-2-yl) (5,5-dioxodibenzo [b, d] thiophen-2-yl) methanone (3.208 g, 8 mmol), 9,9-diphenyl-9,10-dihydroacridine (2.93 g, 8.8 mmol), Pd$_2$(dba)$_3$ (0.15 g, 0.16 mmol), tPBu$_3$ HBF$_4$ (0.18 g, 0.64 mmol), and sodium tert-butoxide (1.92 g, 20 mmol) are added into a 100 mL reaction flask, and pumping with argon and adding anhydrous toluene (40 mL). Under argon atmosphere, the reaction is refluxed overnight. After cooling, it is repeatedly extracted for three times with dichloromethane (DCM) and washed with water for three times, and then dried by using anhydrous sodium sulfate. Next, it is filtrated and concentrated. Finally, it is purified by silica gel column chromatography and petroleum ether/dichloromethane (volume ratio 8:1) is used as eluent to obtain 4.34 g of white solid compound II

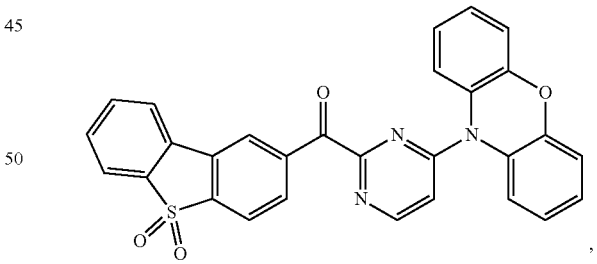

and a yield of product is 83%. Product identification data: HRMS [M+H]+ calcd. for C$_{42}$H$_{27}$N$_3$O$_3$S: 654.18. found: 654.16.

Referring to FIG. 1, it is a photoluminescence spectrum of a thermally activated delayed fluorescent material (compound I and compound II) according to one embodiment of the present invention.

The lowest singlet state (S1), lowest triplet energy level (T1), lowest single triplet energy level difference (ΔEST), highest occupied molecular orbital (HOMO), and lowest unoccupied molecular orbital (LUMO) of the compound I and the compound II are shown in Table 1 below:

TABLE 1

|  | PL Peak (nm) | $S_1$ (eV) | $T_1$ (eV) | $\Delta E_{ST}$ (eV) | HOMO (eV) | LUMO (eV) |
| --- | --- | --- | --- | --- | --- | --- |
| Compound I | 447 | 2.78 | 2.66 | 0.12 | −5.97 | −2.39 |
| Compound II | 449 | 2.76 | 2.96 | 0.07 | −5.97 | −2.37 |

In another embodiment, an organic light emitting diode display device comprises an anode, a cathode, and an organic functional layer disposed between the anode and the cathode. The organic functional layer comprises a thermally activated delayed fluorescent material, and the thermally activated delayed fluorescent material comprises a structural formula (I) as follows:

A-D   (I).

A is an electron acceptor and D is an electron donor, and the electron acceptor comprises any one of following chemical structural formulas:

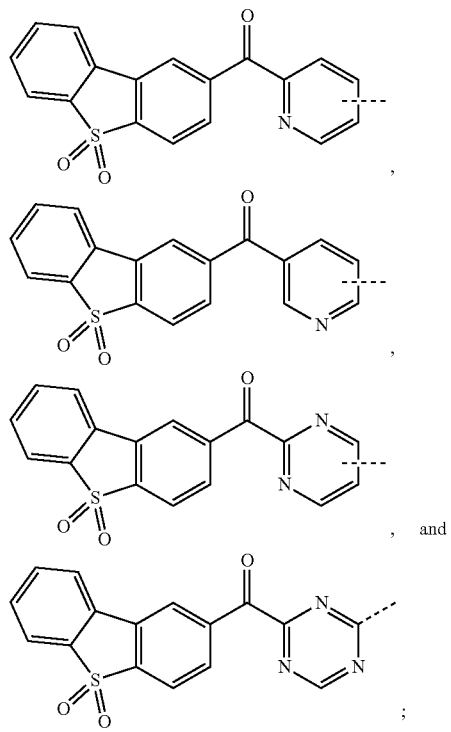

and the electron donor comprises any one of following chemical structural formulas:

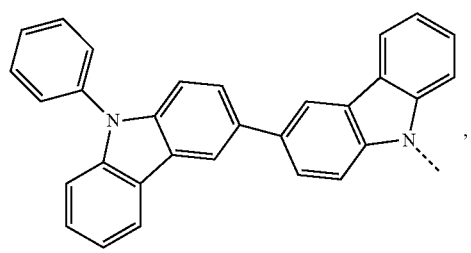

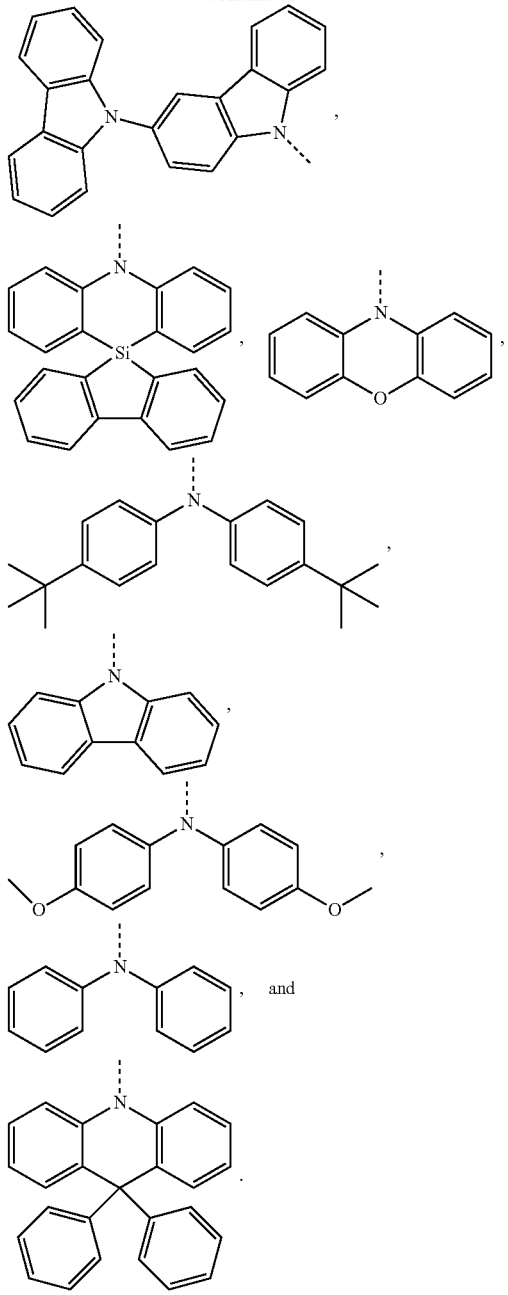

Figure 2:
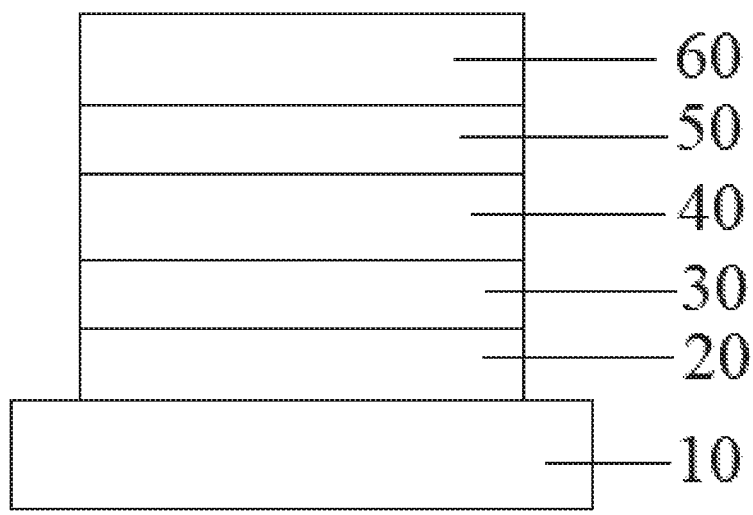
FIG. 2 is a schematic view of an organic light emitting diode display device according to one embodiment of the present invention.

Referring to FIG. 2, it is a schematic view of an organic light emitting diode display device using a thermally activated delayed fluorescent material as a light emitting layer according to one embodiment of the present invention. The organic light-emitting diode device includes a glass substrate and a conductive glass layer 10 made of indium tin oxide (ITO), a hole injection layer 20, a hole transport layer 30, a light emitting layer 40, an electron transport layer 50, and a cathode layer 60. Specifically, the hole injection layer 20 is made of poly 3,4-ethylenedioxythiophene and polystyrene sulfonate. The electron transport layer 50 is made of 1,3, 5-tris(3-(3-pyridyl)phenyl)benzene. The cathode layer 60 is made of lithium fluoride and aluminum. The organic light emitting diode display device can be achieved by a well-known method in the art, so it will not be described again.

Preferably, the fluorescent host material has a structural formula, which is shown as compound I below:

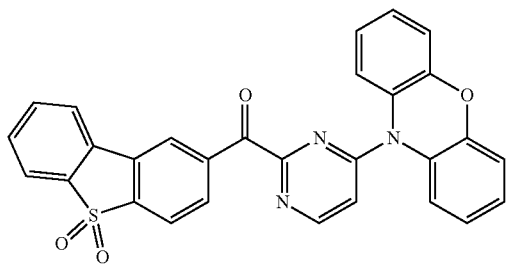

Preferably, the fluorescent host material has a structural formula, which is shown as compound II below:

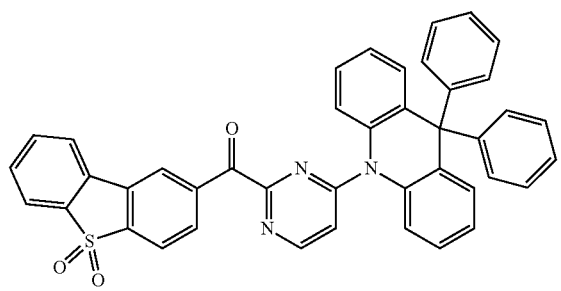

Furthermore, current, brightness, and voltage characteristics of organic light emitting diode display device are achieved by a Keithley source measurement system (Keithley 2400 Sourcemeter, Keithley 2000 Currentmeter) with a silicon photodiode which is calibrated. An electroluminescence spectrum is measured by the French JY SPEX CCD3000 spectrometer, and all measurements are performed at room temperature in the atmosphere.

The compound I is used in the organic light emitting diode display device I, and the compound II is used in the organic light emitting diode display device II, and their performance data are shown in Table 2 below:

TABLE 2

| Device | driving voltage (V) | maximum brightness (cd/m$^2$) | CIEy | Maximum external quantum efficiency (%) | LT95 life time (hrs) |
|---|---|---|---|---|---|
| organic light emitting diode display device I | 3.1 | 2218 | 0.32 | 7.9 | 32 |
| organic light emitting diode display device II | 3.2 | 1985 | 0.35 | 8.2 | 25 |

The thermally activated delayed fluorescent material provided by the embodiment of the present invention can reduce the lowest single-triplet level difference, thereby an organic light emitting diode display device having high luminescent efficiency is achieved.

In the above, the present application has been described in the above preferred embodiments, but the preferred embodiments are not intended to limit the scope of the invention, and a person skilled in the art may make various modifications without departing from the spirit and scope of the application. The scope of the present application is determined by claims.

What is claimed is:

1. A thermally activated delayed fluorescent material, comprising a compound having structural formula (I) as follows:

A-D  (I), wherein A is an electron acceptor, D is an electron donor, and the electron acceptor comprises any one of following chemical structural formulas:

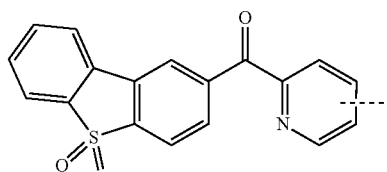

,

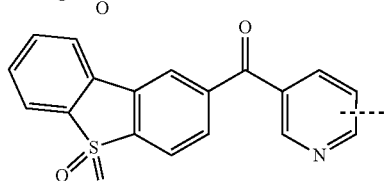

,

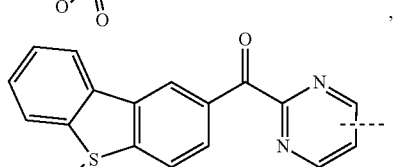

, or

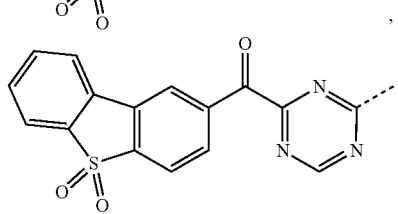

;

and
wherein the electron donor comprises any one of following chemical structural formulas:

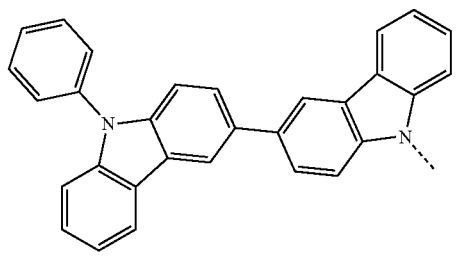

,

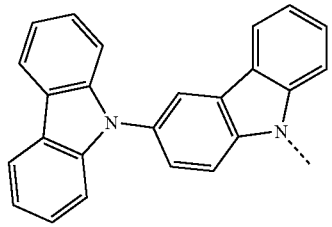

,

-continued
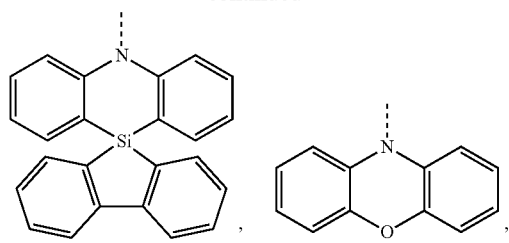 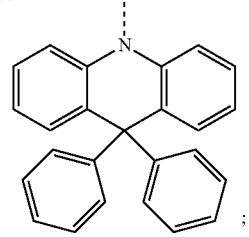
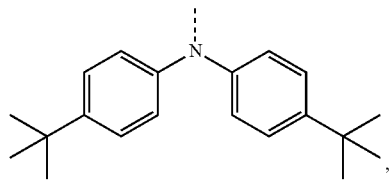
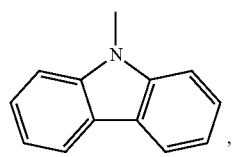
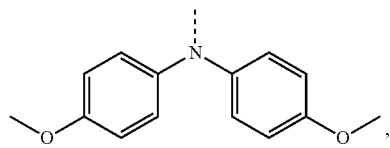
2. The thermally activated delayed fluorescent material according to claim 1, wherein the compound comprises one of following chemical structural formulas:
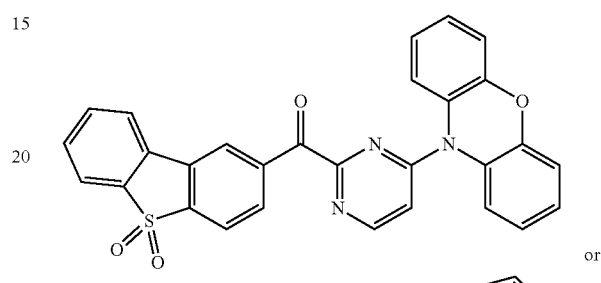
or
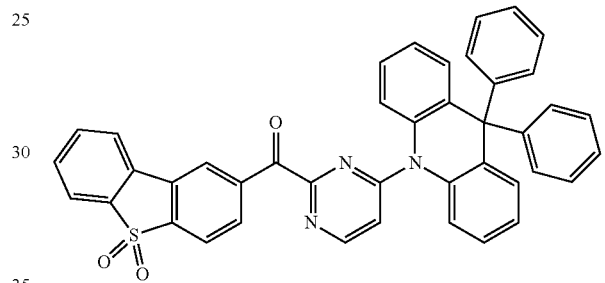
* * * * *